United States Patent
Ulmsten et al.

(10) Patent No.: US 6,645,137 B2
(45) Date of Patent: Nov. 11, 2003

(54) VAGINAL PESSARY

(75) Inventors: Ulf Ulmsten, Dandervd (SE); Jonathan Bennett Gabel, Randolph, NJ (US); Dachuan Yang, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/180,726

(22) Filed: Jun. 27, 2002

(65) Prior Publication Data
US 2003/0149334 A1 Aug. 7, 2003

Related U.S. Application Data (63) Continuation-in-part of application No. 09/677,101, filed on Sep. 29, 2000, now Pat. No. 6,503,190.

(51) Int. Cl.[7] .................................................. A61F 2/00
(52) U.S. Cl. ................... 600/29; 128/834; 128/DIG. 25
(58) Field of Search ............................ 600/29, 30, 32; 128/DIG. 25, 885, 830, 834; 604/279, 515, 517

(56) References Cited

U.S. PATENT DOCUMENTS

| | | |
|---|---|---|
| 4,019,498 A | 4/1977 | Hawtrey et al. |
| 4,139,006 A | 2/1979 | Corey |
| 4,155,991 A | 5/1979 | Schopflin et al. |
| 4,307,716 A | 12/1981 | Davis |
| 4,516,570 A | 5/1985 | Taban |
| 4,579,110 A | 4/1986 | Hamou |
| 4,669,478 A | 6/1987 | Robertson |
| 4,724,832 A | 2/1988 | Strubel et al. |
| 4,823,814 A | 4/1989 | Drogendijk et al. |
| 4,888,074 A | 12/1989 | Pocknell |
| 5,007,894 A | 4/1991 | Enhorning |
| 5,014,722 A | 5/1991 | Bauer |
| 5,036,867 A | 8/1991 | Biswas |
| 5,065,772 A | 11/1991 | Cox, Jr. |
| 5,188,835 A | 2/1993 | Lindskog et al. |
| 5,224,494 A | 7/1993 | Enhorning |
| 5,236,466 A | 8/1993 | Lauterbach |
| 5,355,896 A | 10/1994 | Schulman |
| 5,474,518 A | 12/1995 | Velazquez |
| 5,527,821 A | 6/1996 | Willman et al. |
| 5,603,685 A | 2/1997 | Tutrone, Jr. |
| 5,611,768 A | 3/1997 | Tutrone, Jr. |
| 5,618,256 A | 4/1997 | Reimer |
| 5,722,931 A | 3/1998 | Heaven |
| 5,771,899 A | 6/1998 | Martelly et al. |
| 5,899,909 A | 5/1999 | Claren et al. |
| 6,056,687 A | 5/2000 | Polyak et al. |
| 6,086,909 A | 7/2000 | Harrison et al. |
| 6,090,098 A | 7/2000 | Zunker et al. |

FOREIGN PATENT DOCUMENTS

| | | |
|---|---|---|
| DE | 19829713 | 1/2000 |
| WO | 9505790 | 3/1995 |
| WO | 9842281 | 10/1998 |

*Primary Examiner*—John P. Lacyk (57) ABSTRACT

A vaginal insert has a flexible body either in the form of a belt or a split cylinder. In either case, the insert may be coiled into a coiled state. The body has a reduced diameter when coiled and exhibits a resilient bias toward uncoiling and expanding in diameter from the coiled state. When the insert is inserted into the vagina of a patient, it expands and presses against the vaginal wall. This pressure in itself may be therapeutic, e.g., in treating cystocele and incontinence. A medicament may be conjoined with the insert that is introduced to the patient through contact with the insert. The insert can have a simultaneous mechanical and pharmacological effect, e.g., in the instance of treating incontinence with a drug and pressure. The belt-type body may incorporate mating ridges and grooves to keep the insert in a cylindrical configuration. Latch elements may be incorporated on the insert to support the insert in an expanded, partially uncoiled state.

34 Claims, 8 Drawing Sheets

VAGINAL PESSARY

CROSS REFERENCE TO RELATED APPLICATION

This is a continuation-in-part- to application Ser. No. 09/677,101 entitled "A Vaginal Pessary" and filed on Sep. 29, 2000, now U.S. Pat. No. 6,503,190.

FIELD OF THE INVENTION

The present invention relates to a vaginal device for therapeutic and diagnostic purposes, and more particularly to a resilient vaginal insert that exerts pressure upon the vaginal walls to diagnose and treat various types of pelvic floor defects including urinary incontinence and also to a system for the controlled and sustained delivery of pharmacological compounds for treatment of various diseases inside or outside the genital tract.

BACKGROUND OF THE INVENTION

A significant number of women suffer from urinary stress incontinence, primarily as a consequence of stresses to the musculature of the pelvic floor and ligaments supporting the bladder experienced during childbirth. Surgical remedies and apparatus to aid this condition are known, such as that disclosed in U.S. Pat. No. 5,899,909 relating to a method and apparatus for placing a supportive surgical tape beneath the urethra. Surgery is contraindicated in some patients, however, due to intolerance to anesthesia, preference or other reasons. In addition to surgical treatments for incontinence, it has been known for many years that a suitably proportioned object placed within the vagina proximate to the urethra and/or bladder can be used to support, reposition and/or constrict the urethra and/or bladder to ameliorate incontinence. For example, an inflatable toroidal bladder (U.S. Pat. No. 5,007,894) and a five-sided plate with a U-shaped indentation for supporting/occluding the urethra (U.S. Pat. No. 4,139,006) have been proposed for vaginal insertion to treat incontinence. Certain of the proposed vaginal inserts are formed from resilient material, member with a bladder neck cradle (U.S. Pat. No. 5,036,867) and a folding insert having legs that resiliently urge against the vaginal wall to exert pressure on the urethra (U.S. Pat. No. 5,618,256).

The foregoing apparatus having varying degrees of effectiveness, ease of use, ease of removal, associated discomfort and hygienic impact. Accordingly, it remains an objective in the art to provide a vaginal insert addressing a variety of disorders, such as, urinary incontinence, that is maximally effective, comfortable, easy to use and hygienic.

Further, there are numerous conditions outside and within the genital and/or urogenital tract, such as hormonal dysfunctions, cancer, inflammation, infection or incontinence that may be treated by pharmaceutically active compounds. Many of these compounds are presently orally administered, In certain instances, however, this is a disadvantage, viz., when systemic delivery is used to treat a condition or disease that is more effectively treated by local application. Accordingly, it would be desirable to provide a sustained or controlled drug delivery device that is capable of delivery of the drug for an extended period of time, preferably one week or longer. It would be even more desirable to combine a drug delivery device with an apparatus for treating other clinical ailments.

SUMMARY OF THE INVENTION

The limitations of known vaginal inserts for treating disease are addressed by the present invention, which includes a vaginal insert having a body formed from a flexible material permitting the body to be coiled into a coiled state to form a generally cylindrical configuration. The body exhibits a resilient bias toward uncoiling and expanding in diameter from the coiled state. The insert is insertable into a vagina in the coiled state and is expandable therein to press against the vaginal wall as the body exhibits its resilient bias.

A method in accordance with the present invention for treating disease with a vaginal insert includes coiling the insert into a coiled state; inserting the insert into a vagina; and allowing the insert to expand, thereby contacting and pressing against the interior walls of the vagina.

BRIEF DESCRIPTION OF THE FIGURES

For a better understanding of the present invention, reference is made to the following detailed description of an exemplary embodiment considered in conjunction with the accompanying drawings, in which.

DETAILED DESCRIPTION OF THE FIGURES

Figure 1:
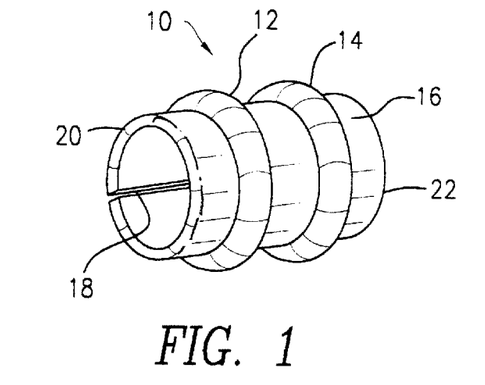
FIG. 1 is a perspective view of a pessary in accordance with a first exemplary embodiment of the present invention.
Figure 2:
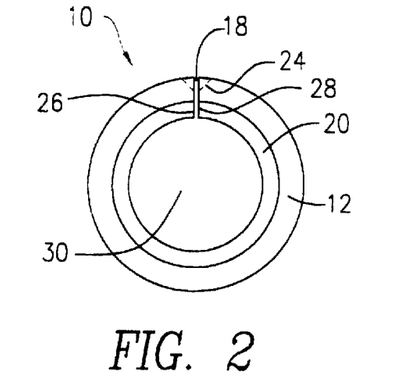
FIG. 2 is a front view of the pessary of FIG. 1.

FIGS. 1 and 2 shown a monolithically formed pessary 10 having a generally cylindrical or tubular configuration. A pair of rings 12, 14 extends radially from the peripheral surface 16. Preferably, the pessary 10 also comprises a longitudinal slit 18, which extends along one side from end 20 to end 22. Longitudinal slit 18 permits the pessary 10 to be coiled for insertion and/or use (see FIG. 3). In addition, longitudinal slit 18 ensures that, when released after insertion, the pessary 10 applies an outwardly directed pressure on the vaginal walls. The ends 20, 22 and the rings 12, 14 are preferably radiused, i.e., are rounded off, rather than having sharp edges for facilitating insertion into and withdrawal from the vagina and avoiding discomfort to the user during use. The pessary is preferably formed from santoprene or silicon or any other resilient material that is bio-compatible, non-absorptive and resists bacterial growth. Pessary 10 may also incorporate a flexible plastic or metal coil incorporated within the flexible material. The flexible metal or plastic material may be, for example, spring metal that allows the pessary 10 to exert additional pressure against the vaginal walls. Further, the pessary 10 may be loaded, impregnated or surface treated with bacteriacides, deodorants or lubricants. In addition, the pessary 10 may be loaded with various pharmacological compounds, such as hormones and/or alpha-adrenoceptor agonists, urethra selective stimulators, prostaglandins, anticholinergics, hormones, nicotine, cytostatics, tranquilizers, local anaesthetics and other compounds, such as pharmacologically active alpha-[tertiary-aminomethyl]-benzenemethanol derivatives and other compounds as disclosed in U.S. Pat. No. 5,527,821 to Willman, et al, which is incorporated by reference herein.

Methods of associating drugs, hormones or other pharmacological compounds with an object for drug administration to the body are well known to those skilled in the art, as for example, described in U.S. Pat. No. 5,188,835 and German Patent No. 198 29 713, both incorporated in their entirety by reference herein. In still a further embodiment, topical medications, ointments or creams can be associated with pessary 10 by infusion (injection), coating or absorption into the pores of a sponge-like material of the medication of the pessary 10 and slowly released, within a day or two, into the vaginal cavity. This embodiment of the invention may be used for treating dryness, irritation or other local conditions. The ointment, cream, etc., can be replenished into the pessary on an as needed basis.

It is preferable that the junction of surfaces, e.g., the junction of the rings 12, 14 with the surface 16, be smooth to aid in cleaning and disinfecting the pessary 10 for reuse. It can be expected that the pessary 10 will stay in place for up to three months. The pessary 10 is configured to be easily removable by the user so that it can be cleaned on a weekly basis using a saline solution or other known hygienic cleaner. In FIG. 2, a relief groove 24 is depicted in dotted lines to avoid the user's vaginal wall from being pinched between the free ends 26, 28 proximate the slit 18. The pessary 10 has a lumen 30 that may be used to grasp the pessary 10 for removal and which allows the vaginal passage to remain open thereby permitting the normal flow of menstrual fluids and the continued use of tampons and other sanitary products.

Figure 3:
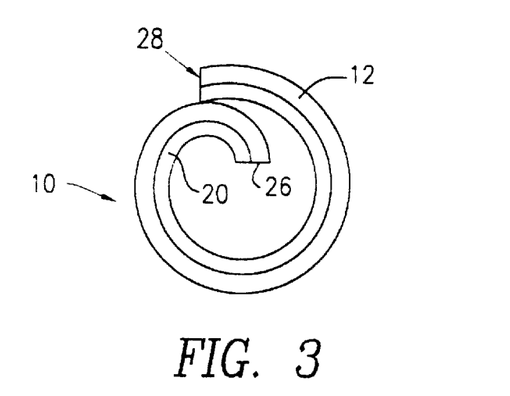
FIG. 3 is a front view of the pessary of FIGS. 1 and 2 in a coiled position.

FIG. 3 shows that the pessary 10 can be coiled to reduce its effective diameter to aid in inserting it into the vagina. In addition, the coiled configuration of the pessary 10 can be utilized as a method of storing energy to maintain an outwardly directed force that presses the outer surface 16 and rings 12, 14 against the vaginal walls to achieve the intended effect on the urethra, i.e., to prevent incontinence, treat various forms of prolapse and/or provide continuous contact between the pessary 10 and the vaginal walls that facilitates a controlled release of drugs from the pessary 10 into surrounding tissue. The size of the pessary 10 can be selected relative to the patient's vaginal dimensions such that when the pessary 10 is coiled to the desired degree, it exerts a selected continuous outward pressure. Since the coiled pessary 10 acts as a spring, it permits contraction and expansion responsive to varying pressure exerted by the vaginal wall due to postural changes, exercise, coughing, etc. The flexibility of the coiled pessary 10 that allows it to adjust dynamically to the patient's bodily movements also minimizes the risk of mucous membrane irritation and/or ulcer formation. The pessary 10 exerts a relatively constant pressure on the urethra thereby avoiding incontinence partly by direct pressure causing an occlusive effect on the urethra and partly by inducing a nerve/muscle reflex mechanism controlling closure of the urethra. In the alternative, the pessary 10 can be used in a manner that permits its complete uncoiling, such that the free ends 26, 28 abut one another, as shown in FIG. 2, preventing recoiling or collapse of the pessary 10 under the influence of the user's vaginal musculature.

With respect to sizing of the pessary 10, it is preferable that a variety of sizes be available to suit the individual requirements of the patient. Providing different sizes of the pessary 10 takes into consideration that each patient has different vaginal dimensions and different requirements in terms of the pressure that the pessary 10 exerts in order to achieve the objectives mentioned herein. It is intended that the present invention be available in a number of sizes, e.g., from about 20 mm to about 60 mm O.D. at surface 16, a length from about 30 mm to about 50 mm from end 20 to end 22, rings 12, 14 having a width of about 2 mm to about 5 mm and a height above surface 16 of about 2 mm to about 5 mm and having a spacing therebetween of approximately 15 mm.

Figure 4:
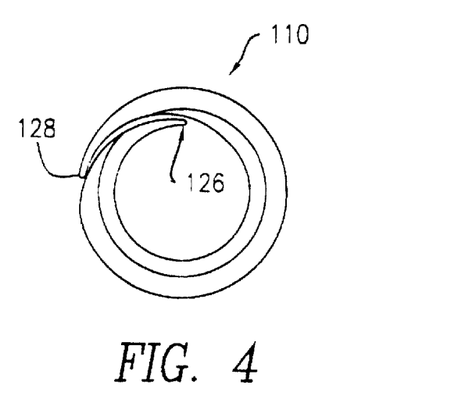
FIG. 4 is a front view of a second embodiment of the present invention.

FIG. 4 illustrates an alternative embodiment 110 of the present invention that has features particularly suitable for a coiled pessary 110. Namely, one or both of the free ends 126, 128 are tapered to allow the coiled pessary 110 to have a smooth outer periphery and to avoid the abrupt ledge that would otherwise accompany a coiled configuration (as shown in FIG. 3). As noted above, it is preferable for all edges to be radiused (rounded) to avoid any irritation to the vaginal lining and to promote comfortable use.

Figure 5:
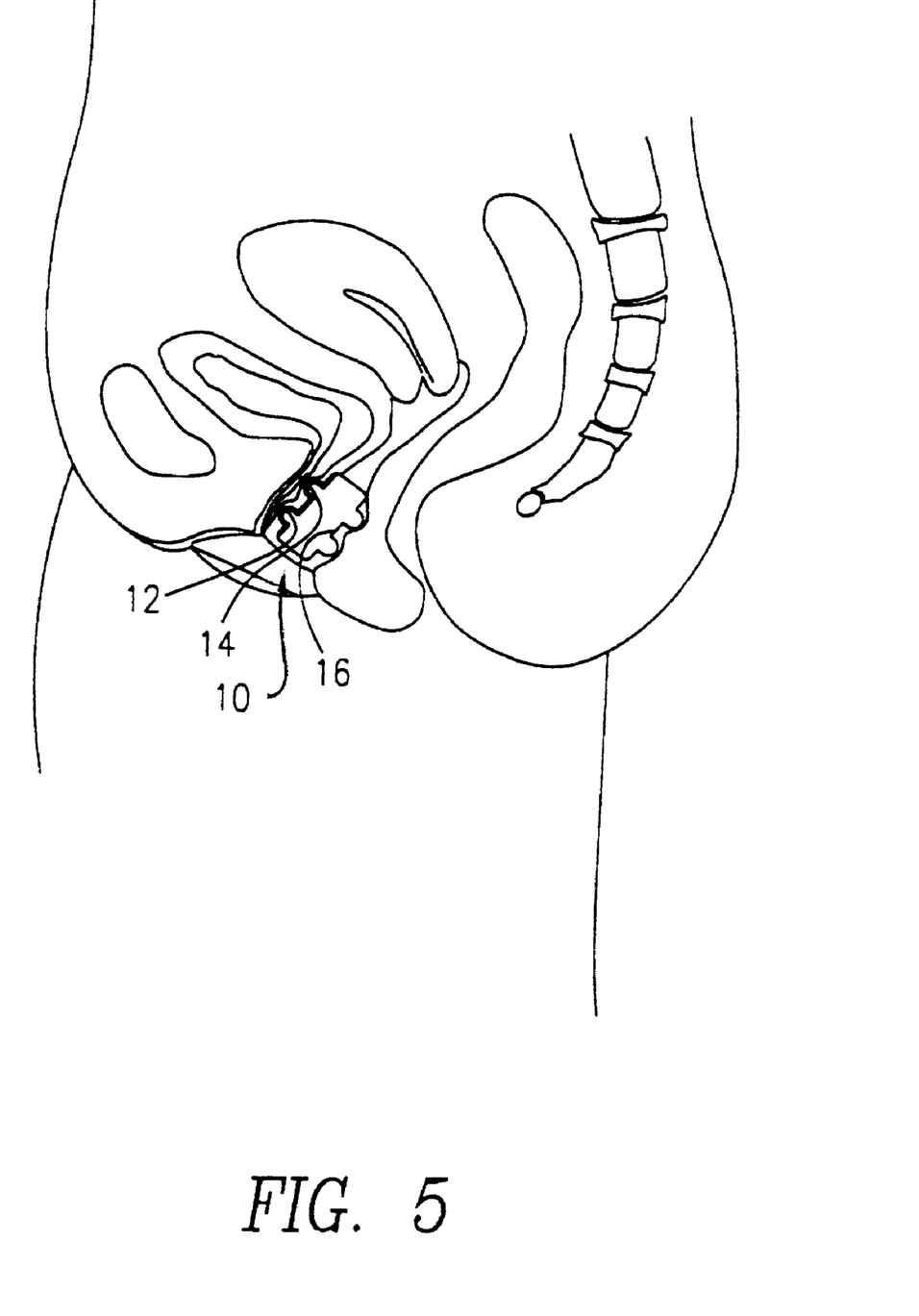
FIG. 5 is a diagrammatic, cross-sectional view of the female urogenital system showing a pessary in accordance with the present invention placed within the vagina.
Figure 6:
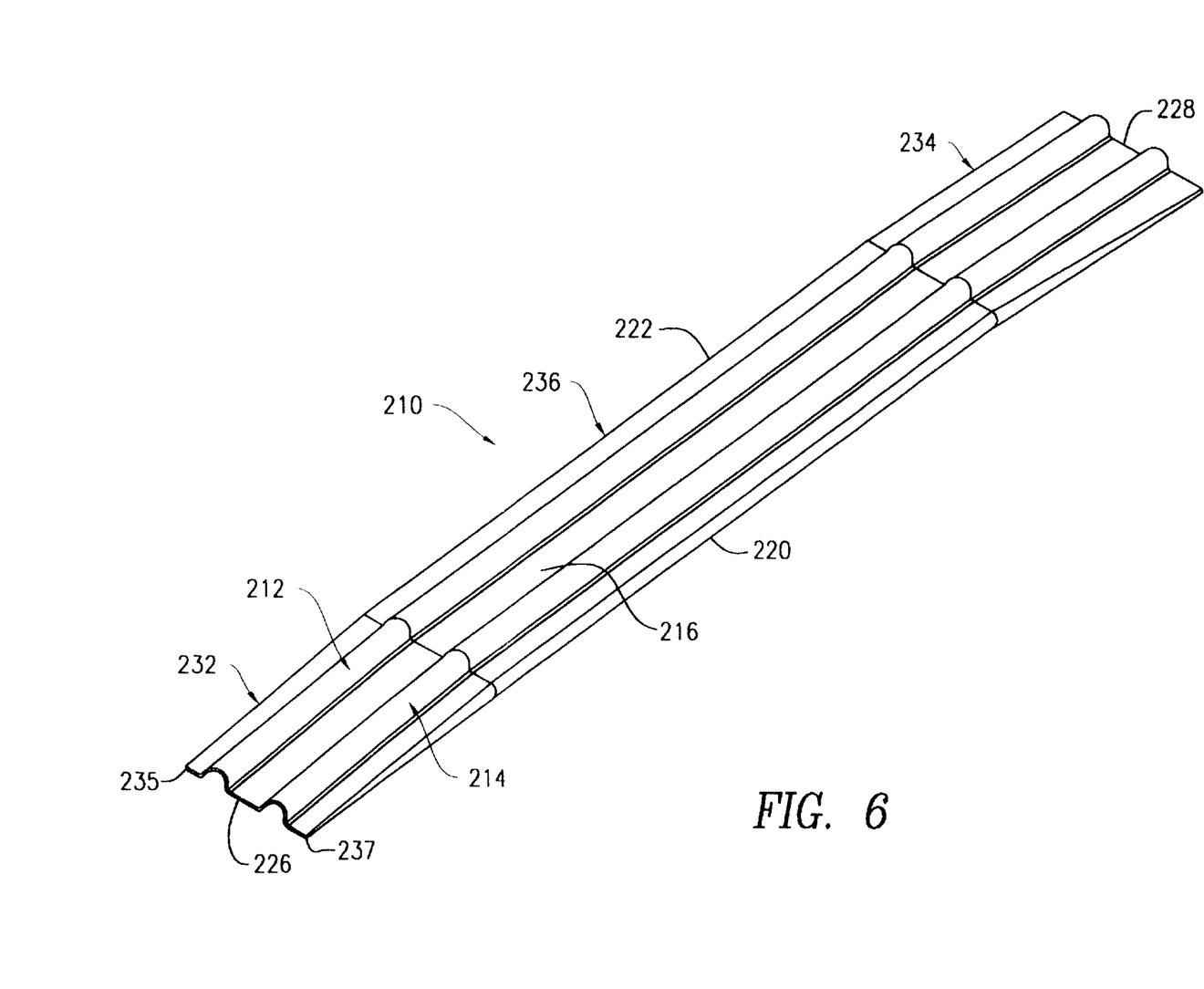
FIG. 6 is a perspective view of a pessary in accordance with a third exemplary embodiment of the present invention in an uncoiled state.
Figures 7, 8:
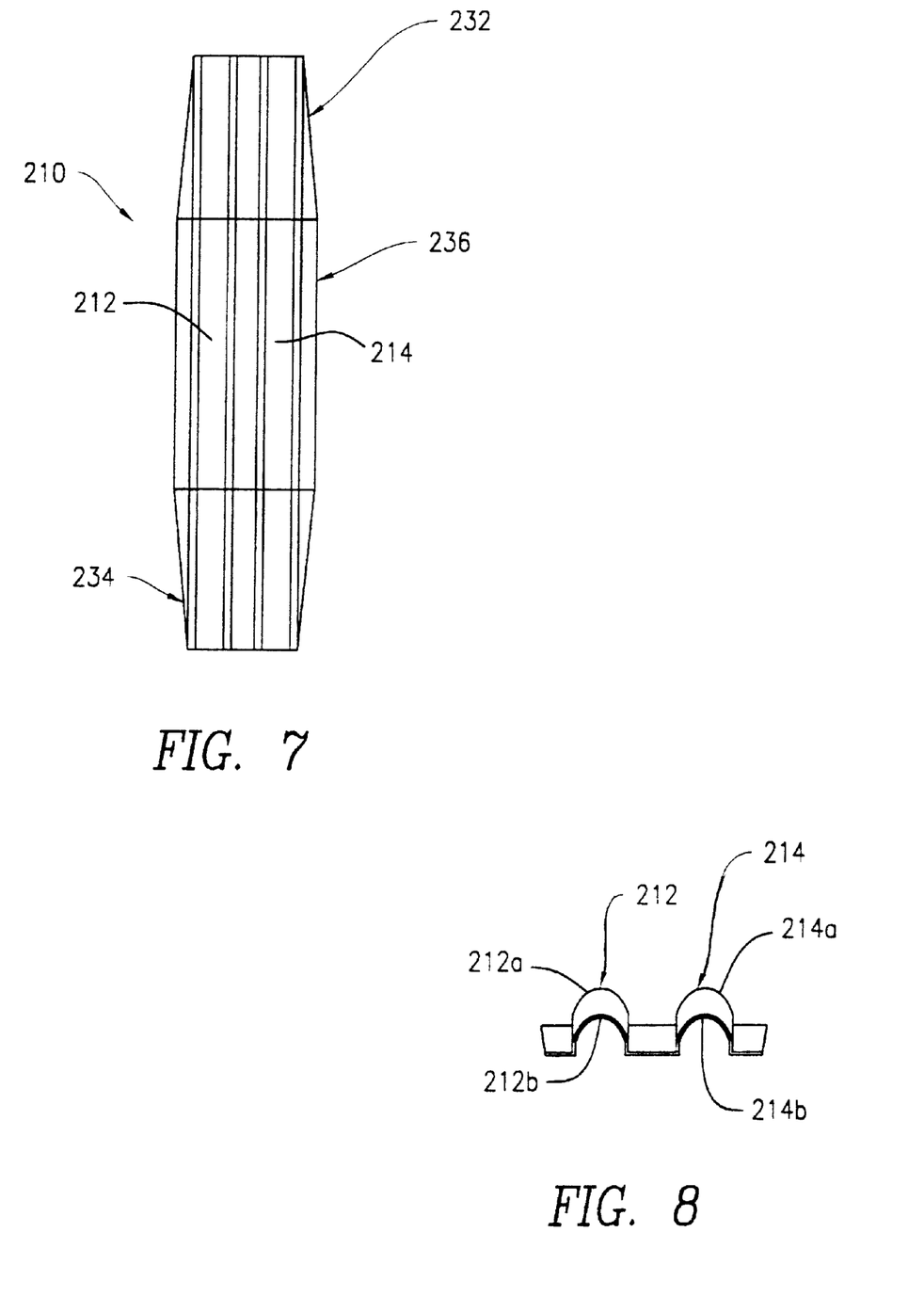
FIG. 7 is a plan view of the pessary of FIG. 6.
FIG. 8 is a side view of the pessary of FIGS. 6 and 7.
Figure 9:
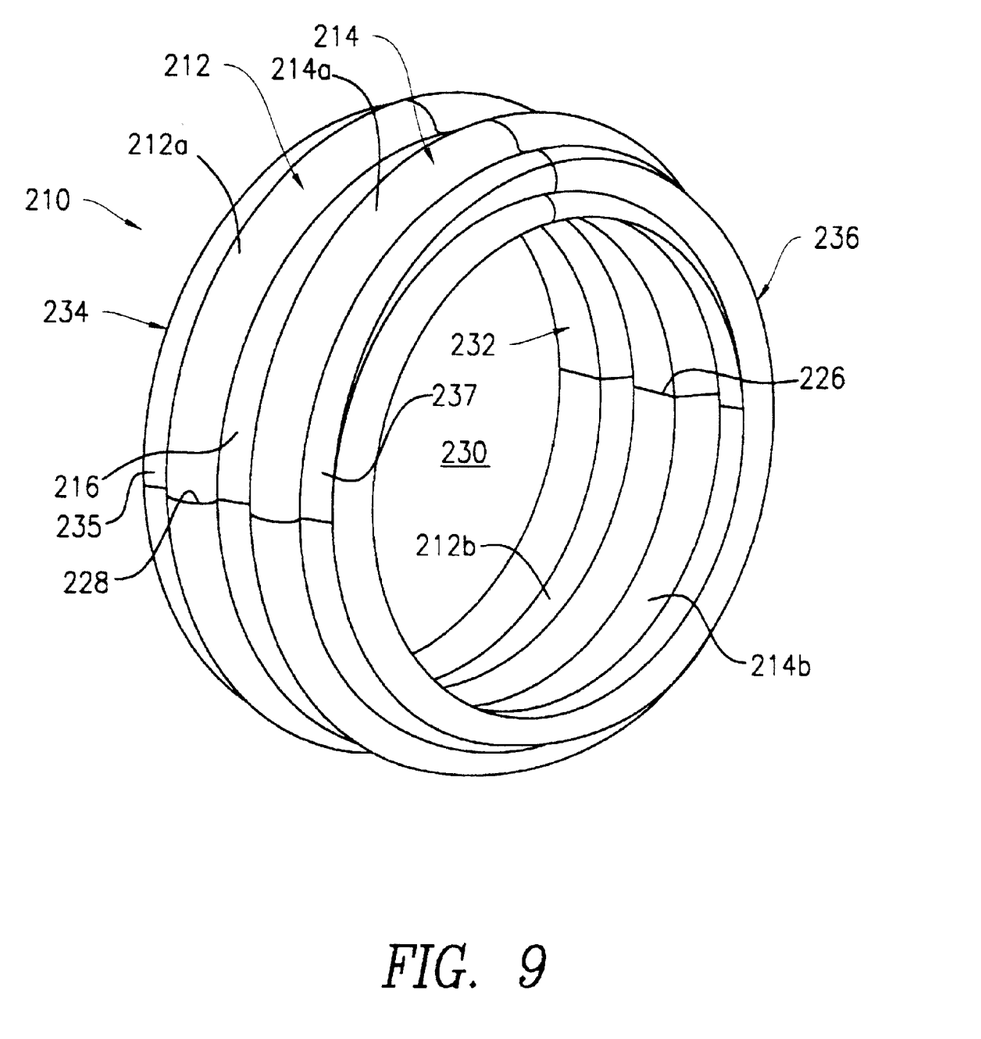
FIG. 9 is a perspective view of the pessary of FIGS. 6 through 8 in a coiled configuration.

FIG. 5 illustrates the pessary 10 in place within the vagina of a user. The diameter of the pessary 10, as delimited by surface 16, is dimensioned to be accepted comfortably within the vagina, without exerting significant force on the vaginal walls. A greater, localized force is exerted by the rings 12, 14. The rings 12, 14 press into the vaginal wall causing the wall to assume a complementary shape and prevent the pessary 10 from sliding axially once placed within the vagina. The displacement of the vaginal wall by the rings 12, 14 displaces adjacent tissue thereby providing the effects previously mentioned. In certain patients, the effect required to treat urinary incontinence necessitates removal of the pessary 10 to allow micturition. The elongated, generally cylindrical configuration of the pessary 10 keeps it oriented axially relative to the axis of the vagina and is comfortable to use due to its complementary shape relative to the vagina and due to the fact that the displacement of the vaginal walls by the pessary is distributed over a large surface area. The fact that the pessary 10 has two rings 12, 14 permits the pessary 10 to work over a greater range of positions, i.e., placement position is not as critical as it would be if only one ring were present. Because the pessary 10 shown is symmetrical, it can be inserted with either end first and it does not matter what rotational orientation is used. Alternatively, the pessary 10 may be asymmetrical having a distal and proximal end.

As would be appreciated by one skilled in the art, the present invention may also be used as a diagnostic tool. That is, a patient can be easily assessed as to whether her incontinence may be treated by providing support below the urethra. The pessary 10 is an inexpensive, non-invasive diagnostic device that provides the surgeon and patient with treatment options without having to perform a surgical procedure. The present invention can therefore be utilized to determine if the patient would be helped by a surgical implant that supports the urethra, such as TVT surgical tape sold by Gynecare, a business unit of Ethicon, Inc., Somerville, New Jersey. In addition, the pessary 10 can be utilized to support a prolapse of the bladder into the vagina for managing a cystocele. Further, since the pessary 10 exerts an outwardly directed force and a corresponding resistance to inward compression, the pessary 10 may be utilized as resistance against which the vaginal and neighboring musculature may be worked, e.g., in training the pelvic floor muscles.

FIGS. 6–9 show a pessary 210 having an uncoiled shape which approximates a rectangle. The rings 212, 214 of the pessary 210 are in the form of a pair of upstanding ridges extending along the length of the pessary 210 and having upper convex surfaces 212a, 214a and lower concave surfaces 212b, 214b, respectively. When the pessary 210 is coiled (see FIG. 9), the concave surfaces 212b, 214b constitute grooves in the inside diameter of the coiled pessary 210 for receiving the convex surfaces 212a, 214a, which constitute ridges on the outer diameter. The convex surfaces 212a, 214a on the outer diameter interlock with the concave surfaces 212b, 214b of the inner diameter, respectively, where the pessary 210 overlaps. In this manner, the overlapping and interlocking concave and convex surfaces 212a, 214a and 212b, 214b, respectively, prevent the coiled pessary 210, in particular ends 232, 234, from twisting out of a generally cylindrical shape. The interlocking surfaces 212a. 212b and 214a, 214b maintain the pessary 210 in a generally cylindrical configuration when it is being inserted, when the pessary 210 is expanding to exert pressure against the vaginal walls and during use. As can be appreciated from FIGS. 6–9, the ends 232, 234 of the pessary 210 are tapered in thickness and width. As in the embodiment of FIG. 4, the taper in thickness minimizes any transition step or ledge where the outer end 228 overlaps the adjacent coiled pessary 210, eliminating the need for rotational orientation of the coiled pessary 210 in the vagina to ensure that the urethra area above the vagina does not fall into the transition step and to avoid any discomfort or stress associated with a prominent, abrupt transition step at end 228. The taper in width of ends 232, 234 avoids the potential lifting and/or folding over of edges 235, 237, e.g., during insertion. Identical tapered ends 232, 234 permit the pessary 210 to be rolled-up (coiled) starting from either end 232, 234.

In addition to the materials mentioned above in describing FIGS. 1 and 2, the pessary 210 may be made from a soft flexible material, such as polyurethane, silicone rubber, latex rubber, polystyrene copolymers or natural rubber. The material of composition and dimensions of the pessary 210 are preferably selected to exert minimal force against the vaginal walls while preserving therapeutic function to avoid conditions arising from a tight fitting pessary, such as irritation, erosion and tissue stretching. The pessary 210 may be used to treat stress urinary incontinence, bladder, uterine and/or rectal/bowel prolapse. Approximate exemplary dimensions for the pessary 210 are: length 4.83 inches, width 1.07 inches, thickness 0.128 inches. As noted above, the pessary 210 ends are tapered in both thickness and width, e.g., tapering in thickness from 0.128 inches to a thickness of approximately 0.03 inches over a length of approximately 1.3 inches and over the same length (1.3 inches) tapering from a width of 1.07 inches to a width of approximately 0.85 inches. The rings 212, 214 run the length of the pessary 210 from one tapered end 232 to the other 234, are approximately 0.5 inches apart and extend approximately 0.12 inches above the peripheral surface 216 centered about the mid line of the pessary 210. The shape of convex surfaces 212a, 214a and concave surfaces 212b, 214b of the rings 212, 214 is constant along their length, more particularly, through the middle section 236 and at the tapered ends 232, 234. All corners, e.g. 235, 237 of the pessary 210, external edges and edges at intersecting surfaces are rounded. Preferably, the pessary 210 may be made in a variety of sizes to accommodate all vagina sizes, with each size being scaled in proportion, e.g., approximately in proportion to the exemplary dimensions previously given. Exemplary sized pessaries 210 would have lengths of approximately 4.83 inches, 6.55 inches and 8.9 inches, with all the other features scaled proportionately.

Figures 10, 11:
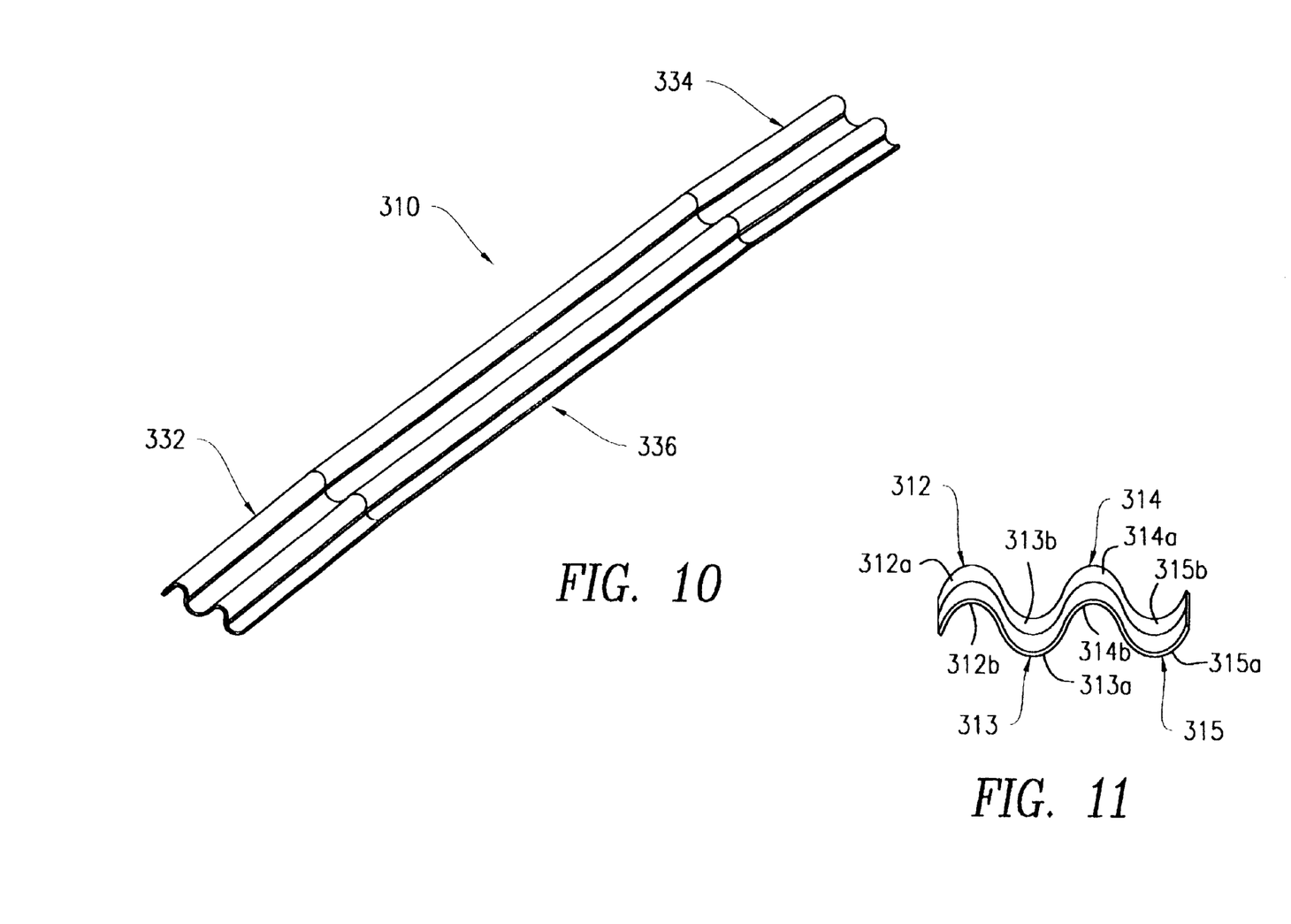
FIG. 10 is a perspective view of a fourth embodiment of the present invention.
FIG. 11 is a side view of the pessary of FIG. 10.

FIGS. 10 and 11 show a pessary 310 having rings 312, 314 with corresponding convex and concave surfaces 312a, 312b, 314a, 314b, respectively. As in the pessary 210, the convex surfaces 312a, 314a and the concave surfaces 312b, 314b constitute ridges and grooves on the outer and inner diameters of the coiled pessary 310 that interlock with each other where the pessary 310 overlaps itself. The pessary 310 has additional rings 313 and 315 disposed on the opposite side of the pessary 310 and laterally offset from rings 312, 314. This provides the pessary 310 with a shape which can be described as having "propeller symmetry". Namely, if the upper surface shape (defined by surfaces 312a, 313b, 314a, 315b) of one side of the pessary is rotated about the long axis of the pessary 310, it constitutes a copy of the opposite side. As in the previous embodiment, the interlocking surfaces, 312a, 312b, 313a, 313b, etc. of the pessary 310 prevent the pessary 310 from twisting out of a generally cylindrical coiled configuration when the pessary 310 is in use or is being inserted. As before, both ends 332, 334 of the pessary are tapered in width and in thickness to minimize any step or ledge formed where the outer ends 326, 328 overlap the adjacent coiled pessary 310 and to avoid undesired folded edges proximate ends 326, 328. As before, the tapered ends 332, 334 are identical, such that the pessary 310 can be rolled up from either end. The propeller symmetry of the pessary 310, however, also allows the user to roll up the pessary 310 from either side in either a clockwise or counterclockwise direction of rotation. Either opposing surface, i.e., the surface having surfaces 312a, 313b, 314a, 315b or the opposing surface having surfaces 312b, 313a, 314b, 315a may be placed in the interior or exterior of coiled pessary 310. Accordingly, there are no specific "inner" or "outer" surfaces, such that there are four ways to coil the pessary 310 due to the symmetries of the pessary 310.

Figure 12:
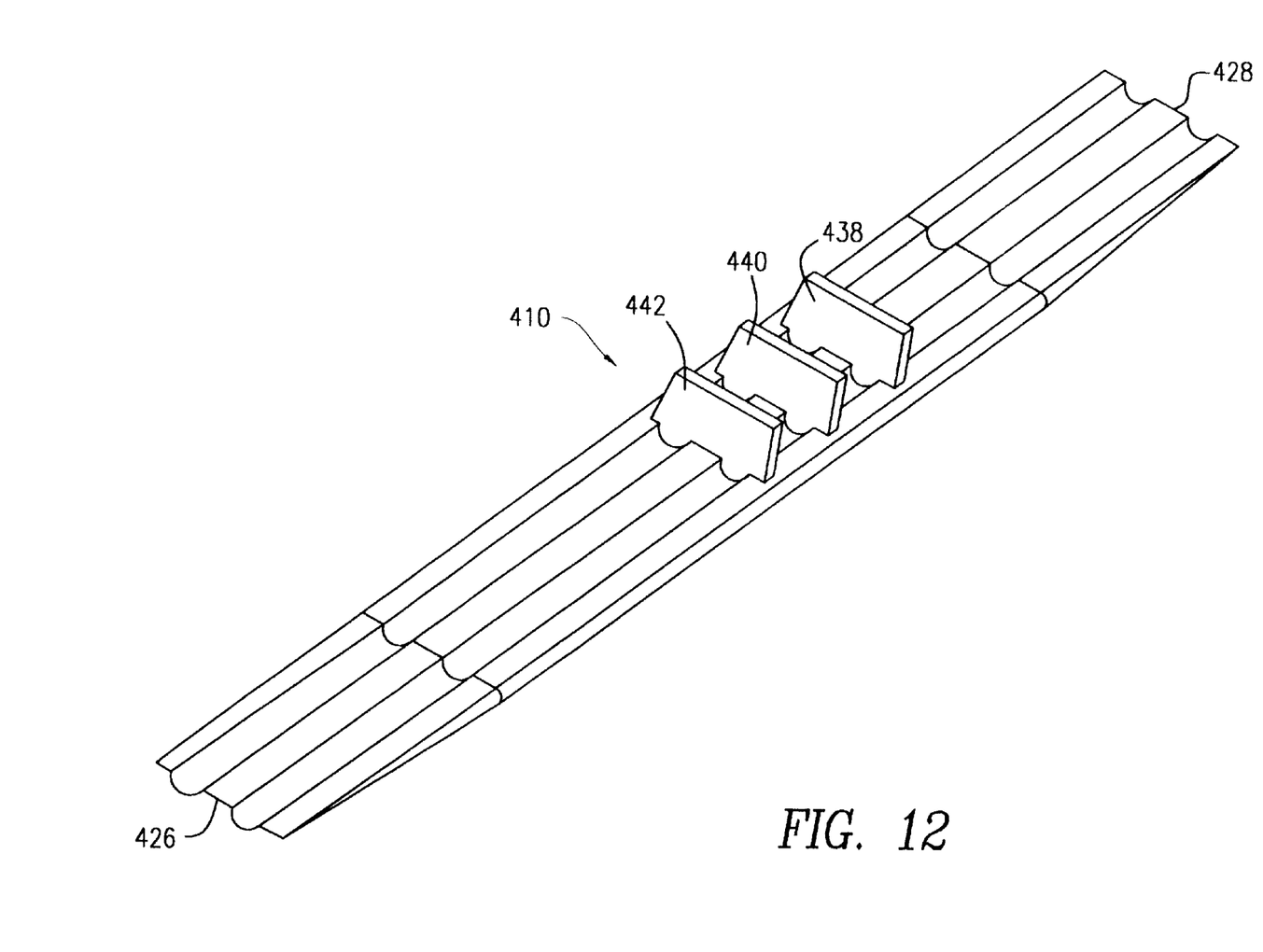
FIG. 12 is a perspective view of a fifth exemplary embodiment of the present invention.
Figure 13:
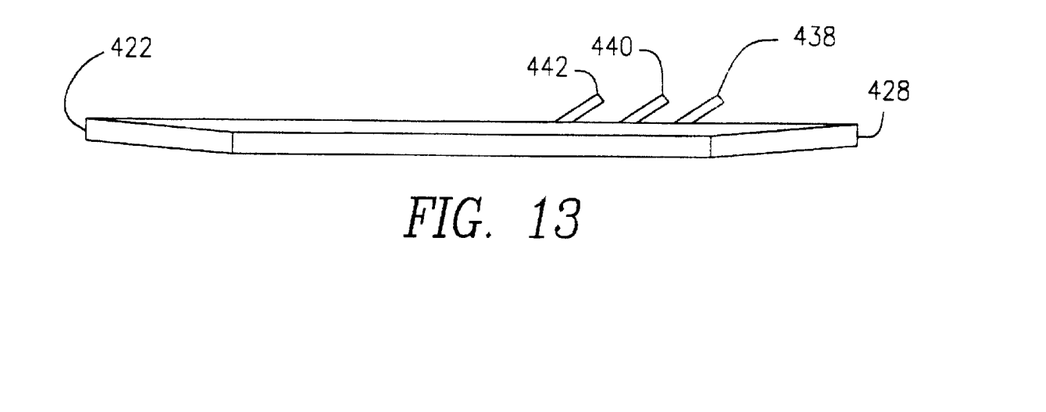
FIG. 13 is a side view of the pessary of FIG. 12.
Figure 14:
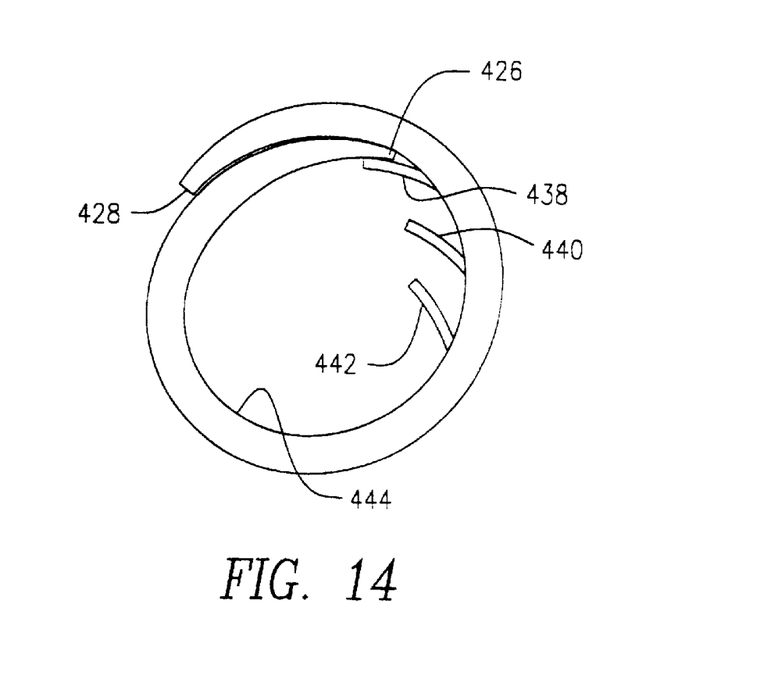
FIG. 14 is side view of the pessary of FIGS. 12 and 13 in a coiled configuration.

FIGS. 12 through 14 depict a pessary 410 having an overall configuration similar to that pessary 210 described in relation to FIGS. 6–11. However, the pessary 410 has a plurality of stops 438, 440 and 442 which prevent inward compression of the pessary (to a more tightly coiled state). More particularly, there are factors that can decrease the outward radial force exerted by a coiled pessary 410 during use, e.g., (1) increased lubricity after the pessary 410 has been infused/coated with bodily fluids; (2) decreased elasticity due to the relaxation of the polymer and material degradation and (3) the release of drugs from the pessary 410 which results in changes to the polymer matrix and its consequent loss of elasticity. A lessening of the outwardly directed radial force exerted by the pessary 410 results in the pessary 410 being compressed and gradually pushed back in the vagina, providing less support and thereby exhibiting a diminishing therapeutic effect. The pessary 410 overcomes this weakening by virtue of the stops 438, 440, 442, as shown in FIG. 14. Namely, when the pessary 410 is rolled into the form of a cylinder and is inserted into the vagina, the resilience of the pessary biases it to an uncoiled condition. As the pessary 410 attempts to uncoil within the vagina, it exerts an outward radial force against the vagina and comes into a state of equilibrium relative to the inward force exerted by the vagina. This state of equilibrium is characterized by a specific position of the end 428 of the pessary 410 relative to end 426. Namely, the more the pessary 410 uncoils, the closer the end 426 approaches end 428. The stops 438, 440, 442 are disposed along the length of the pessary 410 such that the end 426 will be positioned proximate to one of the stops 438, 440, 442 when the pessary 410 is in the equilibrium position. For example, if the pessary 410 were tightly coiled before insertion into the vagina such that end 426 was positioned beyond stop 442 in a direction distal to end 428, as the pessary expands in an uncoiling direction, end 426 slips past stop 442. As shown in FIG. 14, end 426 has slipped past (over) stops 442, 440 and 438. If the pessary 410 shown in FIG. 14 were subjected to inward radial pressure, the end 426 would catch between the stop 438 and the adjacent inner surface 444. In this manner the stops 438, 440, 442 exhibit a ratcheting action relative to the end 426, allowing it to slip past the stops 438, 440 and 442 in the direction of radial expansion (uncoiling) but catching in one of the stops 438, 440, 442 when moved in the direction of radial compression (coiling). As shown in FIG. 14, the stop 438 prevents end 426 from assuming a position wherein the pessary 410 is more tightly coiled and exerts less force on the vaginal walls. Accordingly, the pessary 410 is self locking at the equilibrium position and thereby retains a suitable diameter to maintain treatment, notwithstanding the effects noted above pertaining to lubricity, decreased resiliency due to material degradation or the release of drugs from the polymer matrix. The stops 438, 440, 442 may be formed on the pessary 410 by injection molding, cutting, welding, adhesion or co-extrusion processes. The stops 438, 440, 442 may be of the same material of the pessary 410 body, e.g., polyurethane, silicon rubber, latex rubber, polystyrene copolymers, natural rubbers, etc., or of a different material. Because the self-locking pessary 410 shown in FIGS. 12 through 14 expands to a satisfactory diameter and is then fixed in that supporting position, the pessary 410 may have a reduced thickness while still providing sufficient support for an extended period of time. Because the strength of the materials and/or thickness may be reduced, the pessary 410 is easier to insert and remove and may exert a lesser initial force when first employed, minimizing discomfort and stress.

It should be understood that the embodiments described herein are merely exemplary and that a person skilled in the art may make many variations and modifications without departing from the spirit and scope of the invention as defined in the appended claims. For example, the embodiments described in relation to FIGS. 6–12 may be loaded with a pharmacological compound such as described in relation to the embodiments of the present invention shown in FIGS. 1–5. Accordingly, all such variations and modifications are intended to be included within the scope of the invention as defined in the appended claims.

We claim:

1. A vaginal insert for treating disease of a patient, comprising:
    a body formed from a flexible material permitting said body to be coiled into a coiled state to form a generally cylindrical configuration, said body exhibiting a resilient bias toward uncoiling and expanding in diameter from said coiled state, said vaginal insert being insertable into a vagina in said coiled state and expandable therein to press against the vaginal wall as said body exhibits said resilient bias.

2. The insert of claim 1, wherein said body has an elongated generally rectangular shape when uncoiled.

3. The insert of claim 2, wherein said body has an upper surface, a lower surface and a ridge extending up from said upper surface, said ridge having a convex surface contiguous with said upper surface and a concave surface contiguous with said lower surface, a first portion of said concave surface receiving a second portion of said convex surface therein when said body is coiled.

4. The insert of claim 3, wherein said first portion and said second portion restrain said body from slipping out of a generally cylindrical coiled configuration.

5. The insert of claim 4, wherein said ridge extends lengthwise across said body from one end to another end.

6. The insert of claim 5, wherein said convex surface and said concave surface retain substantially the same cross-sectional shape from said one end to said another end.

7. The insert of claim 5, further including a plurality of ridges.

8. The insert of claim 7, wherein said lower surface displays a propeller symmetry relative to said upper surface.

9. The insert of claim 6, wherein said body has a thickness at either end thereof that tapers.

10. The insert of claim 9, wherein said body tapers in width at either end thereof.

11. The insert of claim 4, wherein said insert is formed from a material selected from the group consisting of, polyurethane, silicon rubber, latex rubber, polystyrene copolymers and natural rubber.

12. The insert of claim 5, further including a medicament conjoined with said body, said medicament transferable from said body to the vagina through contact therewith.

13. The insert of claim 2, further including a latch member extending from said body at an angle, said latch member permitting an end of said body to slidably pass thereover in a direction resulting in the uncoiling of said body but preventing said end of said body from passing said latch member in the direction of coiling once said end has passed thereover in the direction of uncoiling.

14. The insert of claim 13, further including a plurality of latch members arrayed along a length of said body providing a plurality of positions for said end to be restrained, each of said plurality of positions corresponding to an associated degree of uncoiling of said body.

15. The insert of claim 1, further including a medicament conjoined with said body, said medicament transferable from said body to the vagina through contact therewith.

16. The insert of claim 1, wherein said medicament is selected from the group consisting of: alpha-adrenoceptor agonists, urethra selective stimulators, prostaglandins, anticholinergics, hormones, nicotine, cytostatics, tranquilizers, local anaesthetics, alpha-[tertiary-aminomethyl]-benzenemethanol derivatives, bacteriacides, deodorants, lubricants and moisturizers.

17. The insert of claim 1, wherein said medicament is coated on a surface of said body.

18. The insert of claim 1, wherein said medicament is contained in pores in said body.

19. The insert of claim 1, further including a resilient member contained within said body for increasing said resilient bias.

20. The insert of claim 1, further including a ring extending up from an outer peripheral surface of said body.

21. A method for treating disease of a patient with a vaginal insert formed from a flexible material permitting the insert to be coiled into a coiled state to form a generally cylindrical configuration, the insert exhibiting a resilient bias toward uncoiling and expanding in diameter from the coiled state, comprising:

(A) coiling the insert into the coiled state;

(B) inserting the insert into a vagina;

(C) allowing the insert to expand thereby contacting and pressing against the interior walls of the vagina.

22. The method of claim 21, wherein the insert aids in the treatment of incontinence during said step of pressing by causing pressure against the urethra.

23. The method of claim 22, wherein said step of pressing induces a nerve/muscle reflex controlling closure of the urethra.

24. The method of claim 21, wherein said insert has a medicament conjoined therewith, said medicament transferable from the insert to the vagina through contact therewith, and further including the step of transferring the medicament from the insert to the walls of the vagina during said step of contacting.

25. The method of claim 21, wherein said insert has a medicament conjoined therewith, said medicament transferable from the insert to the vagina through contact therewith, and further including the step of transferring the medicament from the insert to the walls of the vagina during said step of contacting, said medicament having a pharmacological effect aiding in reducing incontinence.

26. The method of claim 21, wherein said step of pressing controls the intrusion of a hernia into the vagina.

27. The method of claim 26, wherein the hernia is a cystocele.

28. The method of claim 21, further including the step of the patient controlling her musculature to exert a force against the insert pursuant to a muscle training exercise.

29. The method of claim 24, further including the steps of removing the insert and replenishing the medicament conjoined therewith.

30. The method of claim 21, further including the step of monitoring the physiological effect of the insert upon the patient with respect to her particular disease for the purpose of diagnosis.

31. The method of claim 22, further including the step of monitoring the effect that the insert has upon the patient's incontinence for the purpose of diagnosis and determining efficacy.

32. The method of claim 31, further including the step of removing the insert and selecting a replacement insert having a resilient bias matched to the minimum pressure required to successfully address the patient's incontinence and inserting the replacement insert.

33. The method of claim 32, wherein said step of selecting involves selecting an insert of a particular size from a plurality of inserts in a range of sizes.

34. The method of claim 31, wherein said step of monitoring is pursuant to assessing the patient's amenability to treatment via surgical intervention.

* * * * *